(12) United States Patent
Chattoraj et al.

(10) Patent No.: US 6,329,165 B1
(45) Date of Patent: Dec. 11, 2001

(54) MEASUREMENT AND CONTROL OF SESSILE AND PLANKTONIC MICROBIOLOGICAL ACTIVITY IN INDUSTRIAL WATER SYSTEMS

(75) Inventors: Mita Chattoraj, Warrenville; Michael J. Fehr, Geneva; Steven R. Hatch, Naperville; Robert W. Shiely, Batavia, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/475,585

(22) Filed: Dec. 30, 1999

(51) Int. Cl.[7] .................................. C12Q 1/02; C12Q 1/00
(52) U.S. Cl. ............................... 435/29; 435/968; 435/4
(58) Field of Search ................................. 435/29, 968, 4

(56) References Cited

U.S. PATENT DOCUMENTS

| | | | |
|---|---|---|---|
| 4,783,314 | * 11/1988 | Hoots et al. | 435/29 |
| 5,225,333 | * 7/1993 | Krause et al. | 435/29 |
| 5,702,684 | * 12/1997 | McCoy et al. | 435/29 |
| 5,821,066 | * 10/1998 | Pyle et al. | 435/29 |

* cited by examiner

*Primary Examiner*—Louise N. Leary
(74) *Attorney, Agent, or Firm*—Margaret M. Brumm; Thomas M. Breininger

(57) ABSTRACT

A method for monitoring both the planktonic and sessile microbial populations in an industrial water system by the addition of a fluorogenic dye compound is described and claimed.

15 Claims, 1 Drawing Sheet

Figure 1:
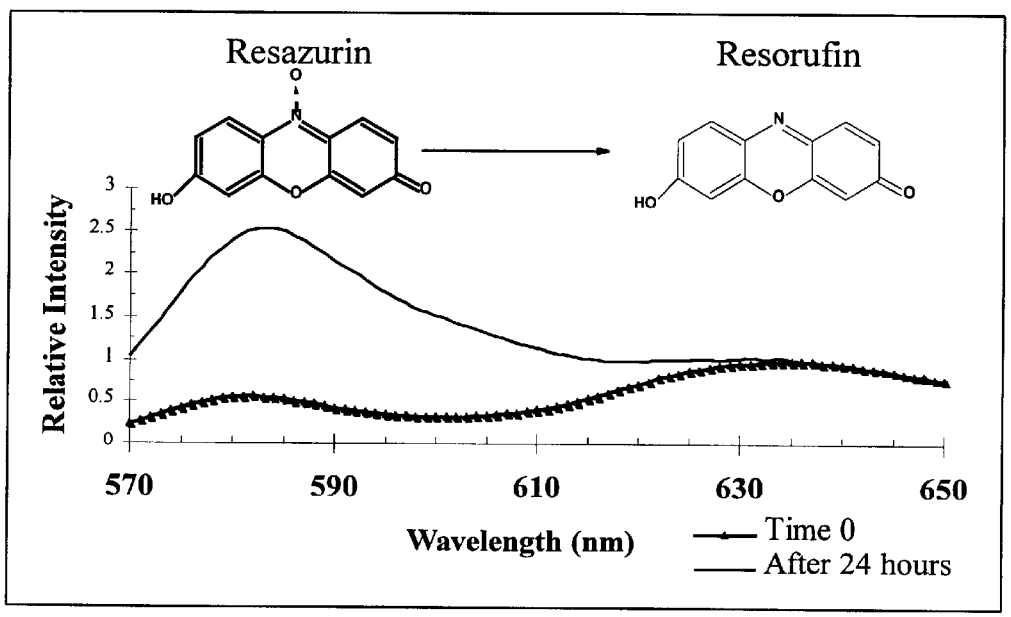

MEASUREMENT AND CONTROL OF SESSILE AND PLANKTONIC MICROBIOLOGICAL ACTIVITY IN INDUSTRIAL WATER SYSTEMS

BACKGROUND OF THE INVENTION

The growth of microorganisms in industrial water systems is a never-ending concern for industry. The accumulation of microbiological organisms and their resulting byproducts often interfere with water processing and manufacturing. In the paper industry, the growth of microorganisms in pulp and paper mill waters can adversely affect finished paper products by spoiling the paper furnish, resulting in quality loss and product defects such as holes and spots. In cooling water systems, the growth of microorganisms can lead to deposits of bacterial colonies on metal parts causing their surfaces to corrode and pit. Additionally, systems are adversely affected by microbial growth by reduced efficiency in heat exchangers and fouling which impedes the functionality of the system.

The conventional method of controlling microbial growth is through the use of biocides. Biocides are chemicals that inhibit microbial growth by destroying the cell wall or cellular constituents of microorganisms. Physical conditions such as temperature, radiation, or assimilation with treatment chemicals contained within a system can have a negative impact on the effectiveness of the biocide. To compensate for the reduced effect, biocides can either be added continuously or judiciously on an as required basis. Judicious use of biocides is encouraged since biocides are both expensive and toxic. Thus, to prevent waste, constant monitoring and testing of the water system is required to determine the proper quantity of biocide for controlling microbial growth.

Known techniques to measure the amount of microbiological activity in an industrial water system include grab sampling and plating techniques. Grab sampling is accomplished by removing an aliquot of water from the system and testing said aliquot off-line. Often the subsequent testing is done off-site as well as off-line. Biocide addition to the water system is adjusted depending upon the results of the sampling.

One grab-sample method involves withdrawing a sample, diluting the sample, and applying the sample to the surface of a nutrient agar medium. After incubation for 24 to 48 hours, the sample is checked for the presence of microorganisms and, where appropriate, the organisms are counted by manual or video means. A variation of this method consists of withdrawing a sample and culturing it for a predetermined time, and then observing the culture medium by nephelometry or turbidimetry. In other words, the presence of microorganisms is revealed by the opacity of the culture medium.

A significant problem associated with grab sampling is the time-lag between withdrawing the sample and completing the analysis to determine the level of microbiological activity in the sample. This time lag can be exacerbated when the samples have to be transported off-site for analysis; further delaying obtaining the results.

In addition to grab sampling, other on-site sampling techniques are available, such as Dip slide and Adenosine Triphosphate (ATP) tests. Unfortunately, such tests are not conducive to instantaneous field readings, given that Dip slides require 24 to 48 hours for test results to develop. ATP tests, although capable of giving results in a short (<2 minutes) time, require reagents needing refrigeration and test equipment which is expensive and often not available in the field. Thus, neither test is optimal for field evaluation of microbiological contamination.

Another problem with grab sampling is that it usually underestimates the overall microbiological activity in the industrial water system because grab sampling is only sufficient to provide an indication of the planktonic microbiological activity, not the sessile activity. Planktonic microbiological populations are alive and exist suspended within the water of an water system. Hereinafter, the term "sessile" refer to populations of microorganisms that are alive, but immobile. It is possible to get an industry-acceptable measurement of planktonic populations by grab sampling since planktonic microorganisms are suspended within the water sample that is removed and tested for microorganism concentrations. In contrast, sessile populations are permanently attached to the structures within the system and their presence is not easily measured by removing a sample of water and testing this sample for microorganisms.

Thus, there is a need for a real-time method capable of monitoring both the planktonic and sessile microbial populations in an industrial water system and using that measurement to control the amount of biocide being added to said industrial water system.

SUMMARY OF THE INVENTION

The first aspect of the instant claimed invention is a process for monitoring of planktonic and sessile microbiological populations in an industrial water system comprising:

a) adding a fluorogenic dye directly into said industrial water system and allowing said fluorogenic dye to react with any planktonic or sessile microbiological organisms present;

b) providing means for measurement of the fluorescent signals of said fluorogenic dye in said industrial water system, with the first fluorescent signal measurement being that of the fluorogenic dye and the second fluorescent signal measurement being that of the reacted fluorogenic dye;

c) using said means for measurement of said fluorescent signals of said fluorogenic dye to measure the fluorescent signal of the fluorogenic dye and the fluorescent signal of the reacted fluorogenic dye, while discarding any measured fluorescent signal values below a predetermined noise level;

d) calculating the Ratio of the measured fluorescent signal of the reacted fluorogenic dye to the fluorescent signal of the fluorogenic dye; and e) monitoring the change in calculated Ratio from step d) to determine the status of the plank-tonic and sessile microbiological populations in the industrial water system.

The second aspect of the instant claimed invention is conducting the process of the first aspect of the instant claimed invention further comprising:

f) determining the optimal amount of biocide to be delivered to the industrial water system wherein said optimal amount is based upon the magnitude of said Ratio or the rate of change of said Ratio; and g) delivering said optimal amount of biocide to the water system.

The third aspect of the instant claimed invention is a process for monitoring of planktonic and sessile microbiological populations in an industrial water system comprising:

a) premixing a predetermined amount of an inert fluorescent tracer material with a predetermined amount of fluorogenic dye to form an inert fluorescent tracer material-fluorogenic dye mixture;

b) adding said inert fluorescent tracer material-fluorogenic dye mixture directly into said industrial water system and allowing said fluorogenic dye to react with any planktonic or sessile microbiological organisms present;

c) providing means for measurement of the fluorescent signals of said inert fluorescent tracer and said fluorogenic dye in said industrial water system, with the first fluorescent signal measurement being that of the fluorogenic dye, the second fluorescent signal measurement being that of the reacted fluorogenic dye and the third fluorescent signal being that of said inert fluorescent tracer;

d) using said means for measurement of said fluorescent signals of said fluorogenic dye to measure the fluorescent signal of the fluorogenic dye, the fluorescent signal of the reacted fluorogenic dye, and the fluorescent signal of the inert fluorescent tracer, while discarding any measured fluorescent signal values below a predetermined noise level;

e) calculating the Ratio of the measured fluorescent signal of the reacted fluorogenic dye to the fluorescent signal of the fluorogenic dye;

f) monitoring the change in calculated Ratio from step d) to determine the status of the planktonic and sessile microbiological populations in the industrial water system;

g) using the fluorescent signal of said inert fluorescent tracer material to determine whether the desired amount of fluorogenic dye is present in said industrial water system; and h) adjusting the amount of fluorescent tracer material-fluorogenic dye mixture added to said industrial water system based on the measured fluorescent signal of said inert fluorescent tracer material.

The fourth aspect of the instant claimed invention is the process of the third aspect further comprising:

i) determining the optimal amount of biocide to be delivered to the water system wherein said optimal amount is based upon the magnitude of said Ratio or the rate of change of said Ratio; and j) delivering said optimal amount of biocide to the water system.

DETAILED DESCRIPTION OF THE DRAWINGS

FIG. 1 shows a plot of Relative Intensity vs. Wavelength (in nm, which stands for nanometers) for a sample of water in a cooling tower. Relative Intensity is a unitless number calculated by dividing each measured fluorescent signal by the measured fluorescent signal at a particular wavelength. In FIG. 1, the particular wavelength chosen was 634 nanometers (hereinafter "nm"). 634 nanometers was chosen because it is the fluorescence emission maxima for Resazurin. Resazurin was added to the water at time zero and allowed to react for 24 hours with any microbiological organisms present. A fluorometer was used to measure the fluorescent signal of the Resazurin and the fluorescent signal of reacted Resazurin, (reacted Resazurin is a compound called Resorufin). Structures of Resazurin and Resorufin are also included in the FIGURE.

DETAILED DESCRIPTION OF THE PREFERRED EMBODIMENTS

The first aspect of the instant claimed invention is a process for monitoring of planktonic and sessile microbiological populations in an industrial water system comprising:

a) adding a fluorogenic dye directly into said industrial water system and allowing said fluorogenic dye to react with any planktonic or sessile microbiological organisms present;

b) providing means for measurement of the fluorescent signals of said fluorogenic dye in said industrial water system, with the first fluorescent signal measurement being that of the fluorogenic dye and the second fluorescent signal measurement being that of the reacted fluorogenic dye;

c) using said means for measurement of said fluorescent signals of said fluorogenic dye to measure the fluorescent signal of the fluorogenic dye and the fluorescent signal of the reacted fluorogenic dye, while discarding any measured fluorescent signal values below a predetermined noise level;

d) calculating the Ratio of the measured fluorescent signal of the reacted dye to the fluorescent signal of the unreacted dye; and e) monitoring the change in calculated Ratio from step d) to determine the status of the planktonic and sessile microbiological populations in the industrial water system.

Initially, a fluorogenic dye compound is added to an industrial water system to be tested and monitored. Typically, the industrial water system contains some type of microbiological organisms. Such industrial water systems include, but are not limited to, cooling towers and boilers, open and closed recirculating systems, including, but not limited to, open once-through systems; waste effluent streams; raw sewage; treated sewage; contaminated ground water; chemical process waters; pulp and paper-making process streams; water-based chemical process streams; fermentation streams; and other non-potable water systems.

In each of these industrial water systems there are expected to be colonies of microbiological organisms in different areas. The level of microbial activity in each of these areas is a function of different factors including initial population of microbiological organisms, aeration, temperature, water flow, the presence of microbial nutrients and the removal of microbial waste. Even in a single section of biofilm the sessile microbial activity will vary across and down the cross-section depending upon the previously available factors. The measured fluorogenic dye response will be a sum total of the response of microbiological organisms in the entire system which are in contact with the flowing water containing the fluorogenic dye. Therefore, even if the level of microbial activity is unusually high in a small section of the heat exchange tube but low everywhere else the fluorogenic dye response may be low. The process of the instant claimed invention measures the averaged microbiological organism activity of the system.

The fluorogenic dye compound added to the industrial water system must be a molecule that undergoes a substantial change in its fluorescent signal on interaction with a broad population of microbiological organisms. Therefore, fluorogenic dyes suitable for use in the instant claimed process must have a detectable fluorescent signal prior to their reacting with microorganism and also must have a different fluorescent signal after they have reacted with microrganisms.

Suitable fluorogenic dyes, include, but are not limited to, acetic acid ester of pyrene 3,6,8-trisulfonic acid;
carboxyfluorescein diacetate,
3-carboxyumbelliferyl β-D-galactopyranoside;
3-carboxyumbelliferyl β-D-glucuronide;
9H-(1,3-dichloro-9,0-dimethylacridine-2-one-7-yl), D-glucuronide;
9H-(1,3-dichloro-9,9-dimethylacridin-2-one-7-yl);
Resorufin β-D-galactopyranoside;
fluorescein di-β-D-galactopyranoside;
fluorescein di-β-D-glucuronide;
Resorufin β-D-glucuronide;
fluorescein diphosphate;
7-hydroxy-3H-phenoxazin-3-one 10-oxide (hereinafter "Resazurin");
7-hydroxy-3H-phenoxazin-3 -one 10-oxide, sodium salt (hereinafter "Resazurin, sodium salt");
methylene blue;
4-methylumbelliferyl phosphate (hereinafter 4MUP);
4-methylumbelliferyl β-D-glucuronide;
pyranine phosphate; and
pyrene 3,6,8-trisulfonic acid 1-phosphate.

The preferred fluorogenic dyes are Resazurin, 4-methylumbelliferyl phosphate (4MUP) and pyranine phosphate. The most preferred fluorogenic dye is Resazurin.

All of these fluorogenic dyes are either commercially available (for example, Resazurin is available as Resazurin, sodium salt, from ALDRICH®, P.O. Box 355, Milwaukee, Wis. 53201, USA, telephone numbers (414) 273-3850 or (900) 962-9591)), or, as is the case with pyranine phosphate, these fluorogenic dyes are capable of being synthesized using procedures reported in the literature.

Fluorogenic dye is added to the industrial water system in an effective amount such that it is capable of determining microbe activity. An effective amount of fluorogenic dye is between about 0.005 ppm and about 1.0 ppm, preferably between about 0.02 ppm and about 0.5 ppm, most preferably between about 0.04 ppm and about 0.1 ppm, and the most highly preferable amount of fluorogenic dye added is 0.05 ppm. When the salt form of the dye, such as Resazurin, sodium salt, is added to the industrial water system, the calculation of ppm is based on the active amount of the fluorogenic dye present.

Of course, the amount the amount of fluorogenic dye used may be greater than these preferred amounts. In fact, the amount of fluorogenic dye added may be up to about 10% of the volume of liquid within the water system. It is believed without intending to be bound thereby that amounts greater than 1.0 ppm will waste fluorogenic dye without providing a commensurate benefit to the system. The prices of the fluorogenic dye also place a practical upper limit on the amount of dye added to the system. Additional factors influencing dye addition to the system include the type of dye, the amount of liquid continuously lost and replenished within the water system and the type of fluids contained within the water system.

The fluorogenic dye is fed either by itself or in combination with an inert fluorescent tracer material or in combination with water treatment agents that are typically fed into a cooling water system such as, but not limited to, scale and corrosion inhibitors.

The meaning of the term "inert", as used herein is that an inert fluorescent tracer is not appreciably or significantly affected by any other chemistry in the system, or by the other system parameters such as metallurgical composition, microbiological activity, biocide concentration, heat changes or overall heat content. To quantify what is meant by "not appreciably or significantly affected", this statement means that an inert fluorescent compound has no more than a 10% change in its fluorescent signal, under conditions normally encountered in industrial water systems. Conditions normally encountered in industrial water systems are known to people of ordinary skill in the art of industrial water systems.

Inert fluorescent tracer materials suitable for use with the fluorogenic dyes that are used in the instant claimed invention must have the property of having their unique fluorescent signal be detectably different than the fluorescent signals of the fluorogenic dye. This means that the fluorescent signal of the fluorogenic dye and the fluorescent signal of the reacted fluorogenic dye must both be detectably different than that of the inert fluorescent tracer material.

Suitable inert fluorescent tracer materials are the mono-, di- and tri-sulfonated naphthalenes, including their known water-soluble salts; and the known sulfonated derivatives of pyrene, such as 1,3,6,8-pyrenetetrasulfonic acid, along with the known water-soluble salts of all of these materials, and Acid Yellow 7 (Chemical Abstract Service Registry Number 2391-30-2, for 1H-Benz(de) isoquinoline-5-sulfonic acid, 6-amino-2,3-dihydro-1,3-dioxo-2-p-tolyl-, monosodium salt (8CI)).

People of ordinary skill in the art know the typical dosage rates for scale inhibitors and corrosion inhibitors.

It is believed, without intending to be bound thereby, that enzymes synthesized by the microbiological organisms within the water system act upon the fluorogenic dyes. This activity causes a change in the fluorescent signal of said dye and by monitoring said fluorescent signal microbiological activity in said water can be monitored. The method of the instant claimed invention is capable of monitoring microbiological activity from both planktonic and sessile populations, in contrast to methods known in the art.

A means for measurement of the fluorescent signals of the fluorogenic dye, the reacted fluorogenic dye and the inert fluorescent tracer material in said industrial water system, includes commercially available fluorometers. A sufficient number of sample means and fluorometers must be used in order to monitor the fluorescent signal of the signal of the fluorogenic dye before it reacts with any microorganisms, the fluorescent signal of the fluorescent dye after it reacts with any microorganisms present, and the fluorescent signal of the inert fluorescent tracer material (if an inert fluorescent tracer material is present).

Measuring the fluorescent signal of both the fluorogenic dye and the reacted dye is a known procedure to someone skilled in the art of fluorometry. For example, the fluroescent properties of fluorogenic dye Resazurin are well known both in its unreacted state and in its reacted "Resorufin" state. It is highly preferred that the sampling means for the fluorometers are located within the industrial water system such that grab samples do not have to be taken. When the sampling means for the fluorometers are located within the industrial water system the type of sampling is typically referred to as in-line measurement.

An in-line measurement is one that is taken without interrupting the flow of the system being measured. Because the sample means for the fluorometer(s) are positioned in-line when conducting an in-line measurement, the sample they are monitoring accurately reflects the entire industrial water system and, as such, the information gleaned from conducting this method accurately reflects both the planktonic and sessile microbiological organism populations. In-line measurement overcomes the problems associated with grab sampling and the need to remove a sample from the aqueous stream for later testing. Also, the reacted and unreacted forms of the dye are tested on a real time basis, wherein an almost instantaneous reading of the Ratio of the two dye populations will provide an indication of microbial activity. Thus, the Ratio's measured rate of change is proportional to the activity of the microorganisms within the system.

Notwithstanding the fact that in-line measurement is the highly preferred way of conducting the method of the instant claimed invention, it is possible to conduct the method of the instant claimed invention using a grab sampling technique suitable to secure samples of the industrial water system. If a grab sampling technique is used, means should be provided to convey the grab sample to the fluorometer in a reasonable length of time such that the data received from the fluorometer accurately reflects the current status of the industrial water system.

The Ratio of the fluorescent signal of the fluorogenic dye to the fluorescent signal of the reacted fluorogenic dye is:

$$\text{Ratio} = \frac{\text{fluorescent signal of reacted fluorogenic dye}}{\text{fluorescent signal of fluorogenic dye}}$$

The Ratio is a unitless number. The Ratio can be calculated manually or with a calculator or with a computer program. For ease of use, it is preferable that the Ratio be calculated using an appropriate computer program such that a record of the Ratio can be continuously calculated at set intervals. The rate of change of the Ratio can then be used to determine the level of microbiological activity in the system.

Computer programs can be written to automatically calculate the Ratio. A person with ordinary skill in the art of writing computer programs would know how to write a computer program that would automatically calculate the Ratio.

Regardless of how the Ratio is being calculated, an operating system can be created out of commercially available components that can be programmed to process the Ratio. This operating system can use the Ratio to operate the controls that physically add biocide to the industrial water system. The computing means within the operating system can be any digital computer such as, but not limited to, a Programmable Logic Controller (PLC), personal computer or other computing device. The biocide feeder can be a simple container for holding a liquefied biocide and a pump. Preferably the pump is capable of delivering a measured amount of biocide to the water system and can be activated manually or by a signal from the computing device to deliver such measured amount.

Regarding the rate of change of the Ratio, it is known that in the absence of biocide, if the Ratio increases, then the level of microbiological activity is increasing. In the absence of biocide if the Ratio decreases, it means that additional dye is being added to the industrial water system.

When the method of the instant claimed invention is conducted in the presence of biocides certain adjustments have to be made. People of ordinary skill in the art know what biocides are used in industrial water systems. Biocides added in response to unacceptable levels of microbial activity include oxidizing and non-oxidizing biocides. Oxidizing biocides include, but are not limited to:

BCDMH (92.5%, 93.5%, 98%), which is either 1,3-dichloro-5,5-dimethylhydantoin and 1-bromo-3-chloro-5,5-dimethyl hydantoin (CAS Registry #16079-88-2) or a mixture thereof;

bleaches, including stabilized bleaches;

bromine, including stabilized bromine;

calcium hypochlorite (CAS Registry #7778-54-3) "Cal Hypo" (68%);

chlorine, including stabilized chlorine (8.34%);

$H_2O_2$/PAA (21.7%/5.1%) which is hydrogen peroxide (CAS Registry #7722-84-1)/peracetic acid (CAS Registry #79-21-0);

hypobromite;

hypobromous acid;

iodine;

organobromines;

NaBr (42.8%, 43%, 46%) which is sodium bromide;

NaOCl (10%, 12.5%) which is sodium hypochlorite (CAS Registry #7681-52-9);

and mixtures thereof.

Non-oxidizing biocides include, but are not limited to,

ADBAC Quat (10%, 40%(CAS Registry #68391-0-5), 80%)—alkyl dimethyl benzyl ammonium chloride, also known as "quat";

ADBAC quat(15%)/TBTO (tributyl tin oxide 5%);

ADBAC(12.5%)/TBTO (2.5%), (ADBAC Quat/bis tributyl tin oxide) (CAS Registry #56-35-9);

carbamates (30%), of formula $T_2NCO_2H$, where $T_2$ is a $C_1$–$C_{10}$ alkyl group;

copper sulfate (80%);

DBNPA (20%, 40%), which is 2,2-dibromo-3-nitrilopropionamide (CAS Registry #10222-01-2);

DDAC Quat (50%) which is didecyl dimethyl ammonium chloride quat;

DPEEDBAC Quat (1%) which is (2-(2-p-(diisobutyl)phenoxy)ethoxy)ethyl dimethyl, dimethyl benzyl;

glutaraldehyde (15%, 45%), CAS Registry #111-30-8;

glutaraldehyde (14%)/ADBAC quat (2.5%);

HHTHT—hexahydro-1,3,5-tris (2-hydroxyethyl)-5-triazine (78.5%);

isothiazolones (1.5%, 5.6%)—a mixture of 5-chloro-2-methyl-4-isothiazoline-3 -one (CAS Registry #26172-55-4) and 2-methy;-4-isothiazoline-3-one (CAS Registry #2682-20-4);

MBT (10%)—methylene bis thiocyanate;

polyquat (20%, 60%), a polymeric quaternary compound; polyamines and salts thereof—polymeric amine compounds;

terbutylazine (4%, 44.7%)—2-(tert-butylamino)-4-chloro-6-ethylamino-5-triazine (CAS Registry #5915-41-3);

TMTT (24%)—tetramethylthiuram disulfide;

and mixtures thereof.

Any combination of the above biocides may be used. Additional biocides may also be used. These additional biocides would include those known to a person of ordinary skill in the art of biocides. The only restriction on choice of biocide is that if the biocide reacts with the fluorogenic dye faster that it reacts with (destroys) the microbes, then it would be unacceptable.

It has been found that all of the fluorogenic dyes suitable for use in the instant claimed invention are susceptible to degradation of varying degrees in the presence of oxidizing biocides. When the method of the instant claimed invention is used in an industrial water system where these oxidizing biocides are present it is important to add the fluorogenic dye to the industrial water system at a point that is as far as possible away from the point where the oxidizing biocide is added to the industrial water system. Even when the fluorogenic dye and the oxidizing biocide are added to the industrial water system at points as far apart as possible it is known that the oxidizing biocide will quench the fluorescent signal of both the fluorogenic dye and the reacted fluorogenic dye. The quenched fluorescent signals cannot accurately reflect the current status of the microbiological activity in the industrial water system. Accordingly, in the presence of oxidizing biocides, the method of the instant claimed invention must take into account this "quenching" phenomena, by not considering any fluorescent signals, unless they quantified above a certain minimum "noise" level. This minimum "noise" level can be determined with reasonable certainty for every aqueous system where the method of the instant claimed invention can be practiced by a person of ordinary skill in the art of fluorometry.

Oxidizing biocides used at a dosage sufficient to kill the microbiological organisms present, leaving little or no excess oxidizing biocide present will not significantly affect the viability of the measured fluorescent signals. Of course, once additional fluorogenic dye is fed and the signal from that fluorogenic dye is measured, the method regains its viability.

Typical non-oxidizing biocides do not quench the fluorescent signal of fluorogenic dyes and reacted fluorogenic dyes. Therefore, if only non-oxidizing biocides are present in an industrial water system it is believed that the fluorescent signals will always accurately reflect the current status of microbiological activity in the industrial water system. Nevertheless, in conducting the method of the instant claimed invention in industrial water systems containing only non-oxidizing biocides, the method must be conducted by also not considering any fluorescent signals, unless they quantified above a certain minimum "noise" level. Again, this minimum "noise" level can be determined with reasonable certainty, for every aqueous system where the method of the instant claimed invention can be practiced, by a person of ordinary skill in the art of fluorometry.

The preferred method of addition is to premix the fluorogenic dye with a scale and/or corrosion inhibitor and add that mixture to the industrial water system. The biocide (whether oxidizing or non-oxidizing or a mixture thereof) is then fed separately.

By calculating the Ratio as opposed to simply measuring an absolute value of fluorescent signals information is obtained that is (1) independent of dye concentration and (2) more sensitive to the microbial activity. The sensitivity is due to the fact that the microbiological organisms convert fluorogenic reagent dye to reacted fluorogenic reagent dye with the Ratio increase being due to both the decrease in the fluorescent signal of the unreacted fluorogenic dye and increase in the fluorescent signal of the reacted fluorogenic dye (the product).

Microbiological organisms commonly found within industrial water systems which thus far have been detectable by and responding to the detection methods of the present process include, but are not limited to, Pseudomonas, Bacillus, Klebsiella, Enterobac, Escherichia, Sphaerotilus, Haliscomenobacter. As mentioned previously this listing is not exhaustive, noting that other bacteria and/or microorganisms may be detectable by the process using said apparatus.

In an alternative embodiment the method of this invention involves measuring the fluorescent signal emitted from an inert fluorescent tracer material as well as the fluorescent signals of the unreacted and reacted flourogenic dye. The inert fluorescent tracer material is used to determine the concentration of fluorogenic dye present and by knowing that concentration it is possible to operate the system so that a desired level of fluorogenic dye is always present. See U.S. Pat. Nos. 4,783,314, 4,992,380, 5,041,386, which are hereby incorporated by reference, for a thorough discussion of the use of inert tracers to account for "hydraulic losses" within industrial water systems.

The alternative method of using an inert fluorescent tracer material requires the concentrations of inert fluorescent tracer material and dye be maintained in proportion to each other within a solution being fed into the water system. The proportion must be maintained such that there is a reference used to determine the change in the Ratio of the detected fluorescent signals from both the inert and fluorogenic dye.

A real time determination of the Ratio enables immediate evaluation of the microbial activity as well as the efficiency of the current biocide dosage and any increase as needed. Real-time determination of biological activity enables the process to add biocide on an as needed basis. Adding excess biocide, greater than what is needed to control the microbial activity is avoided when such dosages can be accessed on a real-time basis. Thus, the use of biocide can be administered at determined effective levels, which results in the correct amount of biocide being used. Additionally, the effectiveness of a biocide feed can be evaluated on a real-time basis and the dosage can be increased or decreased depending upon the real-time reading.

The following examples are presented to be illustrative of the present invention and to teach one of ordinary skill how to make and use the invention. These examples are not intended to limit the invention or its protection in any way.

EXAMPLES

Example 1

An examination of one fluorogenic dye and its fluorescent signal properties as the fluorogenic dye reacts with microbiological organisms.

Example 1a

Investigation of Fluorescent Signal Properties of Resazurin

Resazurin, sodium salt, is available from ALDRICH®. In aqueous systems, the salt dissolves, leaving the Resazurin as a known fluorogenic dye that can react with the respiratory enzyme, dehydrogenase, present in the membrane of many microbiological organisms. Because of this reaction with dehydrogenase, Resazurin is reduced to 3H-phenoxazin-3-one, 7-hydroxy-, also known as Resorufin. Resazurin and Resorufin have different fluorescent signals. The chemical structure formulas for Resazurin and Resorufin can be found in FIG. 1.

Resazurin has a known fluorescent emission signal maximum at 634 nm while Resorufin has a known fluorescent emission signal maximum at 583 nm. The fluorescence emission spectra of a cooling water sample containing 0.2 ppm Resazurin is shown in FIG. 1. These spectra were obtained using a SPEX fluorometer available from Jobin Yvon Spex, 3880 Park Avenue, Edison N.J. 08820. The fluorometer was setup as follows: Bandwidth was set at 2.5 nm for both excitation and emission, the excitation wavelength was set at 550 nm and the emission was scanned between 570 and 650 nm at 1 nm step intervals with 0.2 second integration time at each step.

In FIG. 1, the time zero spectra is shown as the line with triangles. The spectra taken after 24 hours is shown, as the smooth line, in FIG. 1. The time zero spectrum has peaks at both 583nm and 634 nm, indicating the presence of small quantities of Resorufin present within the sample of Resazurin. The sample of Resazurin used had a small quantity of Resorufin present, which means this spectra accurately reflected the composition of the sample at time zero. The 24-hour spectrum also has peaks at 583 nm and 634 nm but the relative intensity of these peaks are considerably different.

The two spectra in FIG. 1 have each been normalized to the intensity at 634 nm. Normalized means the fluorescence counts (i.e. fluorescence intensity) at each wavelength have been divided by the counts at a particular wavelength. Thus, the intensity of the spectrum is relative to the intensity at a particular wavelength. The spectra were normalized at 634 nm, because this spectra was chosen to demonstrate the difference in the form of the spectra and the sample chosen was predominantly Resazurin, which has a fluorescence emission peak at 634 nm. It would also have been possible to normalize these spectra at 583 nm for purposes of this invention.

The change in spectra over the 24-hour time period was due to the interaction of Resazurin with microbiological organisms present in the cooling tower water. Microbial action on the Resazurin converted the Resazurin to Resorufin. Resazurin is reduced by the membrane-bound dehydrogenases present in micro-organisms. Dehydrogenases are a class of electron transfer enzymes present in all microbiological organisms. Without the interaction with the microbiological organisms, Resazurin does not by itself, in real-time, convert to Resorufin, in the absence of reducing agents.

The ongoing interaction with microbiological organisms causes the 583 nm peak to increase in intensity compared to the peak at 634 nm. By calculating the Ratio of the intensity of the 583 nm peak (reacted fluorogenic dye peak) to the 634 nm peak (fluorogenic dye peak) the extent of microbiological activity within the system can be determined.

Example 1b

Discussion of Ratio Limits

The calculated Ratio of the fluorescent signal of a reacted fluorogenic dye to the fluorescent signal of the reacted fluorogenic dye has limiting values. In typical water obtained from a cooling tower (pH of approximately 9.0), the two peaks at 583 nm and 634 nm are similar in intensity for Resazurin. After interaction with the microbiological organisms the Ratio steadily increases. This increase continues proportionately with microbial activity until the value saturates. The value at which the Ratio saturates depends on the sensitivity and calibration of the fluorometer. This is because not all detectors are equally sensitive at 583 nm and 634 nm. For a well calibrated system (The Spex fluorometer) the calculated Ratio saturates at 5. By saturates it is meant that this is the maximum measurable value of the Ratio. The microbial activity may continue unabated for a long period afterwards, and the value would not change. The spectrum of Resorufin (pure) has a Ratio of 5 in its spectrum between the intensity at 583 nm and the intensity at 634 nm. Hence if the concentration of Resazurin is very small, Resorufin's spectra dominates. This is because one molecule of Resorufin has a greater quantum yield of fluorescence compared to one molecule of Resazurin.

The reason for saturation is the following: Resorufin has an emission maximum at 583 nm, however, it also emits slightly at 634 nm. The emission intensity at 634 nm is one-fifth the intensity at 583 nm. Resorufin is also a more fluorescent species than Resazurin (i.e if equimolar amounts of Resazurin and Resorufin are excited at a particular wavelength, in this case 550 nm, the intensity of the fluorescence from Resorufin far exceeds that from Resazurin). As a result, when most of the Resazurin has been converted to Resorufin by the microbiological organisms, the fluorescence intensity Ratio saturates to the value for the Resorufin peak alone.

Example 2

This example shows that the change in Ratio is proportional to biofilm (sessile) growth in the system.

The fluorescent dye used was Resazurin. Water held in a reservoir was continuously recirculated through 10 feet of tubing (hereinafter "the biofilm reactor") using a Cole-Parmer (625 E. Bunker Court, Vernon Hills, Ill. 60061, phone (800) 323-4340) variable flow gear pump model 74011-10. The pressure-drop across this tubing was measured using a—7354 Series Pressure Transducer (0–15 PSI) also obtained from Cole-Parmer).

Water containing a dilute (less than 1 gram/L) amount of Tryptic Soy Broth (available from Difco, 1 Becton Drive, Franklin Lakes, N.J., 07417-1883) was continuously added to the reservoir, while excess water was drained. The holding time for the system was about 30 minutes. The biofilm reactor was inoculated with microbiological organisms while biofilm growth was being continuously monitored by monitoring the pressure drop between the ends of the plastic tubing which is a standard method for determining fouling. Resazurin was then periodically added to the system and the Ratio between Resorufin and Resazurin peaks was measured using the SPEX fluorometer (bandwidth was set at 2.5 nm for both excitation and emission, the excitation wavelength was set at 550 nm and the emission was scanned between 570 and 650 nm at 1 nm step intervals with 0.2 seconds integration time at each step) at regular intervals after the dye addition.

The data shown in Example II Table (below) illustrates the change in the Ratio and the change in the pressure drop over time. At time 0, the system was inoculated with microorganism and the system is thought to be free of biofilm. As microbes proliferated over time in the constant supply of nutrients and water, they adhered to the tube walls and formed biofilm mass. As time passed, this biofilm mass grew in thickness. This thickening biomass increased the resistance to water flow in the tubing resulting in an increase in the pressure drop measured. The Resazurin ratio also registered a continuous increase during this time. This correspondence between the results from the pressure drop transducer and the Resazurin ratio shows that we are able to monitor biofilm activity using the method of the instant claimed invention.

EXAMPLE 2 TABLE

| Time (hours:min.) | Ratio Change | Pressure Change |
|---|---|---|
| 0:00 | 0.30 | 0.33 |
| 3:27 | 0.38 | 0.31 |
| 25:07 | 2.10 | 1.72 |
| 53:02 | 3.41 | 5.84 |

Example 3

The fluorogenic dye's response to populations of both planktonic and sessile microbiological organisms.

Sessile microbiological organism populations are grown as a biofilm in a relatively long piece of plastic tubing through which water containing a dilute amount (less than 0.1 gram/L) of Tryptic Soy Broth, is continuously pumped from a reservoir. The holding time for the water in the system is about 30 minutes. The fluorogenic dye is fed and mixed with the water, after which a sample is quickly extracted of the water/dye mix.

An initial sample (hereinafter SAMPLE PRIME) of water is removed from the tubing and taken to measure the initial fluorescent signal of Resazurin and the fluorescent signal of Resorufin. The fluorometer used to measure the fluorescent signal is a SPEX fluorometer.

SAMPLE PRIME is then kept and periodically the fluorescent signals of Resazurin and Resorufin are remeasured in this sample. A change in fluorescence in SAMPLE PRIME is indicative of the planktonic microbiological activity in the system because SAMPLE PRIME was removed from the tubing and is no longer in contact with sessile microbiological organisms. The time evolution of the Ratio of the fluorescent signal of Resorufin to the fluorescent signal of Resazurin for the initially extracted SAMPLE PRIME shows the growth of planktonic bacteria present in the cooling tower water.

Periodically additional samples are taken from the tubing and the fluorescent signals of the unreacted dye and the reacted dye are measured in these tubing samples so that a Ratio of these signals can be calculated. The Ratio of these signals is indicative of both the sessile and planktonic population combined.

To determine the sessile microbiologically activity in the system, additional samples (SAMPLE 30, SAMPLE 60) are withdrawn from the biofilm reactor and the fluorescent signals of both the unreacted dye and reacted dye are measured within those samples.

A Ratio is determined for each set of fluorescent signal measurements, with said Ratio indicating the microbiological activity.

Each Ratio is linked to either planktonic activity (from Sample Prime) or the sum of the sessile and planktonic activity from the aliquots taken from the biofilm reactor.

However, the large change in the fluorescence ratio observed in the aliquots taken subsequently from the biofilm reactor compared to SAMPLE PRIME indicate the dominance of the biofilm activity over the planktonic activity. Therefore, it has been demonstrated that the Resazurin dye is able to penetrate into the biofilm and respond. The magnitude of the response may be ascribed to the much larger population of active microbes in the biofilm.

EXAMPLE 3 TABLE shows the results of each experiment.

| Example | Concentration of dye (ppm) | Fluorogenic Dye | Time (min) | Ratio in SAMPLE PRIME Sample (planktonic only, no sessile polulation) | Ratio in biofilm reactor SAMPLEs (planktonic and sessile populations) |
|---|---|---|---|---|---|
| 3A | 0.2 | Resazurin | 0 | 1.07 | 1.37 |
| 3A | 0.2 | Resazurin | 30 | 1.23 | 5.2 |
| 3B | 0.2 | Pyranine Phosphate | 0 | 0.146 | 0.146 |
| 3B | 0.2 | Pyranine Phosphate | 60 | 0.195 | 1.54 |

Example 4

This example shows the effectiveness of the in-line real-time method of evaluating a sessile microbiological organism population (also known as a "biofilm") presence and corresponding treatment with biocide was tested.

EXAMPLE 4 Table illustrates a control scheme for controlling biocide feed to the tower using the method of determining a Ratio with Resazurin as the fluorogenic dye. Fluorogenic dye is continuously added at a threshold level of detection to maintain the overall concentration of unreacted dye and its reacted dye product constant in the water. The resultant Ratio of fluorescent signals was monitored and calculated about every 3 minutes. When the increase in the Ratio exceeded a preset Ratio threshold, biocide was released into the system by the action of turning on the biocide pump. The biocide pump remained on until the increase in the calculated Ratio of fluorescent signals stopped. The increase in the Ratio is due to microbial activity and the decrease is in response to the biocide feed.

EXAMPLE 4 TABLE

| Time into experiment | Ratio | Pump State | Comments |
|---|---|---|---|
| 00:00:0 | 1.3838 | off | Biocide pump is off |
| 0:35:00 | 1.8815 | off | |
| 1:10:00 | 1.52 | off | |
| 1:38:00 | 1.75 | off | |
| 2:13:00 | 2.009 | on | Biocide pump turned on |
| 2:55:00 | 2.159 | on | |
| 3:24:00 | 2.22 | on | |
| 3:52:00 | 2.166 | off | Biocide pump turned off |
| 4:27:00 | 2.054 | off | |
| 4:55:00 | 2.027 | off | |

During this test aliquots were taken at regular intervals and plated to determine the actual amount of planktonic microbiological contamination. The average value, measured using the standard "plate" test, was $3.2 \times 10^3$ colony forming units (abbreviated "cfu"/ml. This value is low enough to indicate overall control of microorganisms in effect throughout this test.

Example 5

Computer Control

Throughout this example the fluorogenic dye used is Resazurin.

These rules are applied in establishing computer control. In this example, the industrial water system selected was a cooling tower.

The parameters used in setting up the computer program are as follows:

Microbial activity causes the ratio to increase by reacting with Resazurin.

Non-oxidizing biocides kill microbiological organisms but do not interact with the dye and cause the ratio to stabilize.

Excess oxidizing biocide reacts with Resorufin and causes the ratio value to decrease.

Blowdown of the tower results in feeding fresh dye to the system causing a decrease in the ratio by increasing the concentration of Resazurin.

The product of the reaction of Resazurin with micobiological organisms is Resorufin. The measured ratio is the ratio of the fluorescent signal of the Resorufin to the fluorescent signal of the Resazurin. The control algorithm described below controls a pump duty cycle proportionally based on the measured ratio with respect to user defined ratio control limits, with consideration of the historical trend in the ratio measurements.

The fluorescent signals at 583 nm (Resorufin) and 634 nm (Resazurin) are measured regularly at a finite user defined measurement interval. These readings are stored in an historical data structure (FIFO list). If the Resorufin and Resazurin measured fluorescent signal intensities are both above user defined threshold values for a user defined minimum number of consecutive measurements, the ratios of these values are used to determine a trend by fitting them to a second order polynomial. If either of the intensities are not above the threshold value for the minimum number of consecutive measurements, no control operation occurs until the next measurement. (This takes care of fluorescent signals that must be discarded due to interaction between the fluorogenic dye and any oxidizing biocides present.) The quality of the fit is determined by a standard Chi-square criterion. If the fit fails the Chi-square test, no control operation occurs until the next measurement. If the slope of the $2^{nd}$ order fit evaluated at the current time is below a user defined minimum value, no control operation occurs until the next measurement.

If the slope of the $2^{nd}$ order fit meets or exceeds the user defined minimum value, control is established by setting the biocide pump duty cycle to a fraction of the measurement interval proportional to the measured ratio's position relative to user defined upper and lower ratio limit values. If the measured ratio is below the lower ratio limit, the biocide pump remains off. If the measured ratio is above the upper ratio limit, the biocide pump duty cycle is set to its maximum value. At no time does the biocide pump duty cycle exceed the measurement interval.

The present method has been described in an illustrative manner. Many modifications and variations are possible in light of the above teachings. It is, therefore, to be understood that within the scope of the appended claims the invention may be practiced otherwise than as specifically described.

What is claimed is:

1. A process for monitoring of planktonic and sessile microbiological populations in an industrial water system comprising:
   a) adding a fluorogenic dye directly into said industrial water system and allowing said fluorogenic dye to react with any planktonic or sessile microbiological organisms present;
   b) providing means for measurement of the fluorescent signals of said fluorogenic dye in said industrial water system, with the first fluorescent signal measurement being that of the fluorogenic dye and the second fluorescent signal measurement being that of the reacted fluorogenic dye;
   c) using said means for measurement of said fluorescent signals of said fluorogenic dye to measure the fluorescent signal of the fluorogenic dye and the fluorescent signal of the reacted fluorogenic dye, while discarding any measured fluorescent signal values below a predetermined noise level;
   d) calculating the Ratio of the measured fluorescent signal of the reacted fluorogenic dye to the fluorescent signal of the fluorogenic dye; and
   e) monitoring the change in calculated Ratio from step d) to determine the status of the planktonic and sessile microbiological populations in the industrial water system.

2. The process of claim 1, further comprising:
   f) determining the optimal amount of biocide to be delivered to the industrial water system wherein said optimal amount is based upon the magnitude of said Ratio or the rate of change of said Ratio; and
   g) delivering said optimal amount of biocide to the industrial water system.

3. The process of claim 1, wherein said fluorogenic dye is selected from the group consisting of Resazurin, 4-methylumbelliferyl phosphate (4MUP), and pyranine phosphate.

4. A process for monitoring of planktonic and sessile microbiological populations in an industrial water system comprising:
   a) premixing a predetermined amount of an inert fluorescent tracer material with a predetermined amount of fluorogenic dye to form an inert fluorescent tracer material-fluorogenic dye mixture;
   b) adding said inert fluorescent tracer material-fluorogenic dye mixture directly into said industrial water system and allowing said fluorogenic dye to react with any planktonic or sessile microbiological organisms present;
   c) providing means for measurement of the fluorescent signals of said inert fluorescent tracer and said fluorogenic dye in said industrial water system, with the first fluorescent signal measurement being that of the fluorogenic dye, the second fluorescent signal measurement being that of the reacted fluorogenic dye and the third fluorescent signal being that of said inert fluorescent tracer;
   d) using said means for measurement of said fluorescent signals of said fluorogenic dye to measure the fluorescent signal of the fluorogenic dye, the fluorescent signal of the reacted fluorogenic dye, and the fluorescent signal of the inert fluorescent tracer, while discarding any measured fluorescent signal values below a predetermined noise level;
   e) calculating the Ratio of the measured fluorescent signal of the reacted fluorogenic dye to the fluorescent signal of the fluorogenic dye;
   f) monitoring the change in calculated Ratio from step d) to determine the status of the planktonic and sessile microbiological populations in the industrial water system;
   g) using the fluorescent signal of said inert fluorescent tracer material to determine whether the desired amount of fluorogenic dye is present in said industrial water system; and h) adjusting the amount of fluorescent tracer material-fluorogenic dye mixture added to said industrial water system based on the measured fluorescent signal of said inert fluorescent tracer material.

5. The process of claim 4 further comprising:
i) determining the optimal amount of biocide to be delivered to the water system wherein said optimal amount is based upon the magnitude of said Ratio or the rate of change of said Ratio; and
j) delivering said optimal amount of biocide to the water system.

6. The process of claim 2 wherein said biocide is an oxidizing biocide.

7. The process of claim 2 wherein said biocide is an non-oxidizing biocide.

8. The process of claim 2 wherein said biocide is a mixture of oxidizing and non-oxidizing biocide.

9. The process of claim 1 wherein said fluorogenic dye is Resazurin.

10. The process of claim 1 wherein said Ratio is calculated using a computer program.

11. The process of claim 5 wherein said biocide is an oxidizing biocide.

12. The process of claim 5 wherein said biocide is a non-oxidizing biocide.

13. The process of claim 5 wherein said biocide is a mixture of an oxidizing and non-oxidizing biocide.

14. The process of claim 1 wherein said means for measurement of the fluorescent signal is positioned in-line.

15. The process of claim 1 wherein said means for measurement of the fluorescent signal is positioned off-line.

* * * * *